United States Patent [19]
Dobbie

[11] Patent Number: 5,118,195
[45] Date of Patent: Jun. 2, 1992

[54] AREA SCAN CAMERA SYSTEM FOR DETECTING STREAKS AND SCRATCHES

[75] Inventor: William Dobbie, Manlius, N.Y.

[73] Assignee: RKB Opto-Electrics, Inc., Syracuse, N.Y.

[21] Appl. No.: 579,462

[22] Filed: Sep. 10, 1990

[51] Int. Cl.$^5$ ...................... G01N 21/55; G01N 21/89
[52] U.S. Cl. ...................... 356/430; 250/572
[58] Field of Search ...................... 356/429, 430, 431; 250/562, 572

[56] References Cited

U.S. PATENT DOCUMENTS

| | | | |
|---|---|---|---|
| 2,547,623 | 4/1951 | Cockrell | 356/431 |
| 3,096,443 | 7/1963 | Laycak | 250/562 |
| 3,135,867 | 6/1964 | Daneff | 356/431 |
| 3,754,146 | 8/1973 | Chow | 356/239 |
| 4,013,367 | 3/1977 | Nagao et al. | 356/431 |
| 4,274,748 | 6/1981 | Burtin et al. | 356/431 |
| 4,665,317 | 5/1987 | Ferriere et al. | 356/430 |
| 4,779,005 | 10/1988 | Arnold | 250/578 |

Primary Examiner—Richard A. Rosenberger
Attorney, Agent, or Firm—Salzman & Levy

[57] ABSTRACT

The invention features a real time system for detecting streaks or scratches which occur substantially parallel to the direction of motion of a continuous web of material. The system can also be used to inspect sheets of material that may have been cut from such webs. An energy source such as an incandescent lamp or a bank of lamps generates electromagnetic energy that impinges upon the continuous web of material. CCD cameras receive reflected specular radiation from the web and generate video signals. The CCD cameras are disposed opposite the energy source and within 5° of the plane perpendicular to the continuous web plane. Alternatively, the energy sources may transmit energy through the web material, which energy can be received by the CCD cameras. A processor is connected to the CCD cameras to process the video signals and to generate an enhanced signal-to-noise ratio signal that represents a streak or scratch on the web.

10 Claims, 9 Drawing Sheets

| SEVERITY | CHANNEL | CAMERA | START | END | TOTAL |
|---|---|---|---|---|---|
| Narrow | 9 | 41 | 1617 | 2366 | 749 |
| Wide | 9 | 44 | 3278 | 3833 | 555 |
| Medium | 13 | 63 | 4671 | 5780 | 1109 |
| Medium | 6 | 27 | 6842 | 7609 | 767 |
| Narrow | 11 | 53 | 7955 | 8387 | 432 |
| Wide | 2 | 6 | 9467 | 10202 | 735 |
| Narrow | 13 | 64 | 11052 | 11849 | 797 |
| Wide | 8 | 38 | 12257 | 13060 | 803 |
| Narrow | 6 | 27 | 13938 | 15038 | 1100 |
| Medium | 4 | 19 | 15571 | 16607 | 1036 |
| Wide | 6 | 26 | 17615 | 17883 | 268 |
| Narrow | 6 | 25 | 18157 | 18904 | 747 |
| Wide | 5 | 21 | 19127 | 20229 | 1102 |
| Narrow | 4 | 17 | 20437 | 21087 | 650 |
| Narrow | 14 | 68 | 21475 | 22212 | 737 |
| Narrow | 11 | 50 | 22418 | 23057 | 639 |
| Medium | 13 | 64 | 23918 | 24655 | 737 |
| Medium | 15 | 74 | 25760 | 25947 | 187 |
| Medium | 12 | 55 | 26167 | 26971 | 804 |
| Medium | 2 | 9 | 27473 | 27848 | 375 |

AREA SCAN CAMERA SYSTEM FOR DETECTING STREAKS AND SCRATCHES

BACKGROUND OF THE INVENTION

The present invention relates to systems for detecting defects on a continuous, moving web of material and, more particularly, to detecting web defects in the form of streaks or scratches.

In the field of continuous sheet material manufacture and, in particular, paper manufacture, large, high speed machines manufacture and process paper in continuous webs. It is not unusual for commercial machines in mills to produce or coat paper that is 15 to 30 feet wide. The paper web itself moves at a rate of 3000 feet per minute during manufacture and up to 3500 feet per minute during coating.

The processing of paper on these continuous, industrial machines requires cutting blades, instruments and fixtures that may damage the paper itself. Paper is, of course, a delicate substance by nature, but high speed machines are made of metal and other non-resilient materials. Added to the inherent fragility of the paper may be coated surfaces for photographic, radiographic, xerographic or other uses, which coating or emulsion is even more delicate. Moreover, the coating process itself relies on a coating hopper feed slot or coating bead, which is susceptible to entraining air and entrapping it in the work product itself, affecting the coating thickness.

It is possible and even likely that defects and irregularities attributable to misaligned machine components will become manifest on the paper product itself. Not only may blades be defective, but contamination or particulate matter may become trapped between the blade and the working surface. Even such seemingly innocuous elements as oversized silver grains or gelatin slugs may contribute to undesired production of so-called pencil streaks.

When a machine element does contact the paper, the result is usually not merely an isolated defect, but a streak or scratch that runs along the entire, endless length of the web. Such occasional events are not entirely preventable, as a practical matter, and must be corrected immediately upon detection. Due to the speed of the machinery, each second from detection to correction results in 50 feet of defective paper product.

Unfortunately, defects such as streaks and scratches that run along the major axis of web material have been difficult or impossible to detect during the processing thereof. The problem of streaks and scratches has received considerable attention, of course, but a consistent, highly accurate approach to detecting such defects has not been found. While certain technology has permitted the detection of isolated defects, such as dust particles in a coated layer or air bubbles causing dry spots or holes, subtle scratches have eluded detection.

In U.S. Pat. No. 4,779,005 issued to Jack L. Arnold, a focal plane electronic system is disclosed, in which a two-dimensional array of photo-detectors receives pixel information from a scanned scene. Each pixel is observed by a plurality of detectors, and their signals are summed by time delay and integration circuitry. The system is included in a Z-type, three-dimensional focal plane module. High frequency noise due to spots and other localized anomalies, however, cannot be eliminated.

U.S. Pat. No. 4,274,748 issued to Jean Burtin et al teaches a system by which streaklike defects in running webs and sheets are identified by transversely and repeatedly scanning adjacent lateral sections of the webs or sheets by means of sweeping radiant energy, such as a moving radiation spot. Thus the scanner is adapted to move perpendicular to the direction of the web motion. Transmitted or reflected radiation is received on corresponding photocells that produce a plurality of discrete, successive measurement signals representative of a defect in the webs or sheets. The signal-to-noise ratio of the measurement signals is increased by multiplicative correlation, on the condition that the ratio of the signal component to the effective noise component of the measurement signal is greater than one.

U.S. Pat. No. 3,754,146 issued to Allan TitShing Chow discloses a detecting head and light source which synchronously traverse on opposite sides of a continuous moving web. Photoelectric detector elements are recessed in rectangular channels disposed symmetrically about rectangular coordinate axes. The principal axis of the rectangular channels is in the direction of web travel. A streak defect in a coated layer on the web interferes with the transmitted light to the detecting elements, resulting in an electrical characteristic signal across the detecting elements. The signal is processed for verification of the presence of a streak defect.

The present invention exploits the use of video technology to solve defect problems. It is interesting to note that none of the foregoing references incorporates a video camera for detecting streaks or scratches on a moving web, relying instead on one or more photodetectors to accomplish that purpose. Discrete photocells are used instead. In the case of the aforementioned Arnold patent at least, charge coupled devices (CCD's) are specifically excluded due to their alleged inefficiency.

One of the difficulties in using video images, and perhaps the one to which Arnold alludes, is processing data by means of a technique called "frame grabbing," in which an entire video image is analyzed, pixel by pixel. Although this technique is used extensively in satellite photography, its use in real time paper flow manufacture and processing is limited. This technology is simply too slow to address the machine speed verses resolution problems in commercial paper manufacture. More generally, computerized imaging is inherently a batch process, not suitable for real time continuous processing of paper. Frame grabbing technology is also memory intensive, since each frame contains hundreds of thousands of pixel values which must be processed by computer while keeping up with the machine. An alternative has been to statistically inspect the web material, but such an approach is not acceptable to manufacturers who guarantee uniform, defect-free products. In the case of photographic paper, for example, stringent quality standards specify that even the most subtle streaks cannot be tolerated.

It would be advantageous to provide a high-speed, real time system for detecting defects and irregularities, such as streaks and scratches, in moving webs of material.

It would also be advantageous to detect streaks and scratches on a high speed paper coating or paper production machine.

It would be also advantageous to inspect 100% of processed paper for such defects as a part of quality assurance and control program.

It would also be advantageous to inspect moving webs or material continuously, rather than statistically or repeatedly.

It would also be advantageous to incorporate the use of area scan cameras to detect such defects.

It would also be advantageous to detect streaks and scratches on or in a web of material by using a technique of specular energy reflection.

It would also be advantageous to provide a system for processing video signals to result in a meaningful, suitable display.

SUMMARY OF THE INVENTION

In accordance with the present invention, there is provided a real time system for detecting streaks or scratches which occur substantially parallel to the direction of motion of a continuous web of material. The system can also be used to inspect sheets of material that may have been cut from such webs. An energy source such as an incandescent lamp or a bank of lamps generates electromagnetic energy that impinges upon the continuous web of material. CCD cameras receive reflected specular radiation from the web and generate video signals. The CCD cameras are disposed opposite the energy source and within 5° of the plane perpendicular to the continuous web plane. Alternatively, the energy sources may transmit energy through the web material, which energy can be received by the CCD cameras. A processor is connected to the CCD cameras to process the video signals and to generate an enhanced signal-to-noise ratio signal that represents a streak or scratch on the web.

BRIEF DESCRIPTION OF THE DRAWINGS

A complete understanding of the present invention may be obtained by reference to the accompanying drawings, when taken in conjunction with the detailed description thereof and in which.

DESCRIPTION OF THE PREFERRED EMBODIMENT

Figure 1:
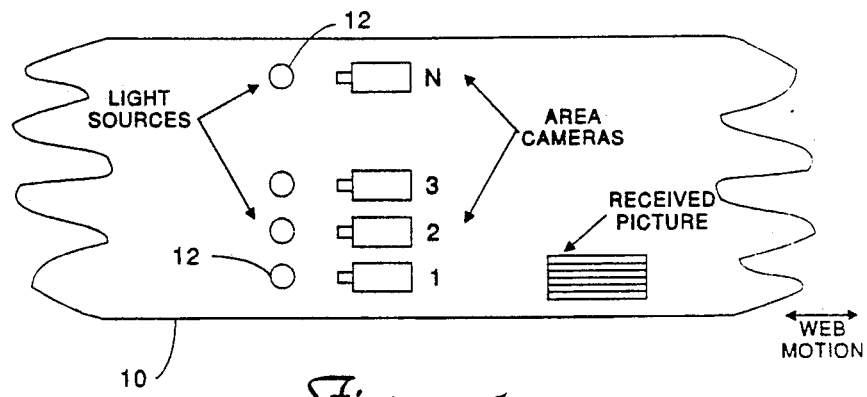
FIG. 1 is a top view of light sources and cameras of the present invention as they are oriented with respect to an inspected web.

Referring now to FIGURE I, there is shown a top view of a web of material and apparatus for inspecting it. A web 10 is provided of sheet material, such as paper, coated paper, plastic or any other materials susceptible to being stored on rolls and manufactured or processed continuously. A number of energy sources 12 is disposed and mounted by conventional means well known in the art in a one dimensional array transverse to the direction of web motion, depicted by the arrow in FIG. 1. Energy sources 12 may be fluorescent, incandescent, infrared, or ultraviolet lamps or suitable sources capable of generating electromagnetic energy. In the preferred embodiment, visible white light sources such as flood lights provided by the Red Dot Company as model no. 110 R30/FL/RS are used. It should be understood that, although a plurality of sources 12 is depicted in the figure, a fewer number or even one continuous light source could be used to illuminate web 10, if used with appropriate optic components such as mirrors and lenses, known in the art. The invention is not intended to be limited to the light source configuration shown and described herein.

Oppositely disposed to light sources 12 is a plurality of area scan cameras 14, labelled respectively camera number 1, camera number 2, . . . , camera number N. The cameras 14 used in the preferred embodiment are model no. SE302 area scan CCD cameras manufactured by the Elmo Company. Cameras 14 are mounted relative to web 10 by conventional means well known in the art and are oriented 90° from their standard operating positions so that the normally horizontal TV raster lines are parallel to the direction of motion of web 10. It should be noted that cameras 14 are shown colinear in the figure, but may be staggered or arranged in any other suitable fashion as long as their cumulative fields of view cover the entire width of web 10 and each field of view overlaps its adjacent fields.

Figure 2:
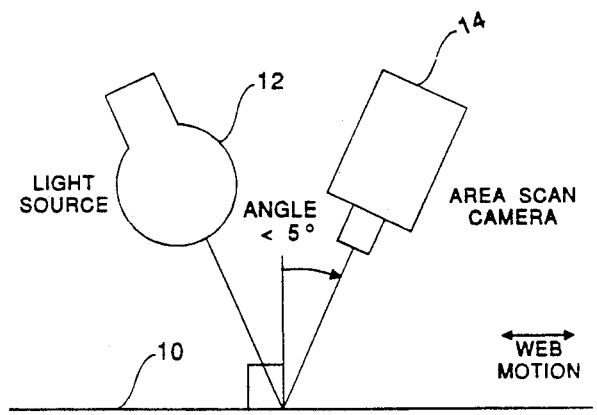
FIG. 2 is a schematic side view of a single light source and camera with respect to the inspected web.

Referring now also to FIG. 2, there is shown a schematic side view of one light source 12 and one area scan camera 14, oriented with respect to web 10. Although not drawn to scale, it can be seen that camera 14 is disposed within 5° of the plane perpendicular to the plane of web 10. The angle of camera 14 relative to the plane of web 10 is critical, in order to minimize keystoning of the received picture, whereas the angle of light from light source 12 impinging upon web 10 need not be within the 5° aforementioned. However, when the light source 12 is greater than 5° offset from the plane perpendicular to the plane of web 10, diffused reflection may occur, rather than specular reflection, which is desired. Moreover, light source 12 must be positioned on opposite side of web 10 to area scan camera 14 when incorporating transmissive lighting, in which light is transmitted through the web material 10.

The overall system design enables the use of a 2" field of view (FOV) in the transverse web motion (machine) direction of each camera 14 and 2.7" FOV in the web motion (machine) direction. Dividing a 2" FOV by 525 lines results in an effective 4 mil resolution. A plurality of CCD cameras 14 is placed on 2" centers, nominally, but they can be moved closer to or farther away from one another, depending on the specific application or desired defect resolution. The placement of 180 CCD cameras 14 in this fashion, across an entire 30-foot web 10, is required to ensure 100% inspection thereof.

Figure 3:
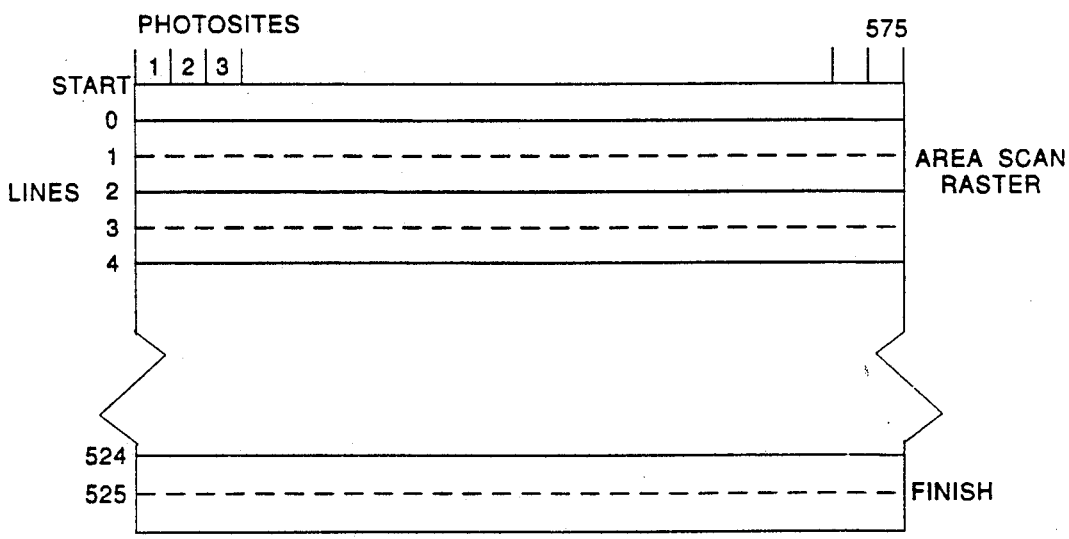
FIG. 3 is an image of a video picture received by the CCD camera.

Referring now also to FIG. 3, there is shown a conventional television raster scheme depicting interlaced odd and even fields and 525 raster lines, formed every 1/60 of a second, producing a standard picture frame every 1/30 of a second. Shown horizontally in the figure are 575 photo-sites or pixels as used in the present invention.

A conventional area scan CCD camera 14 with a two-dimensional array of photo-sites (pixels) detects light being reflected or transmitted by target web 10 over an area field of view, to aid in detecting subtle line phenomena not otherwise discernable. The array consists of 575 pixels horizontal by 525 pixels vertical. No special optics are utilized, except for a standard focusing lens (25 mm, 50 mm, 75 mm, etc.) for CCD camera 14.

Figure 4:
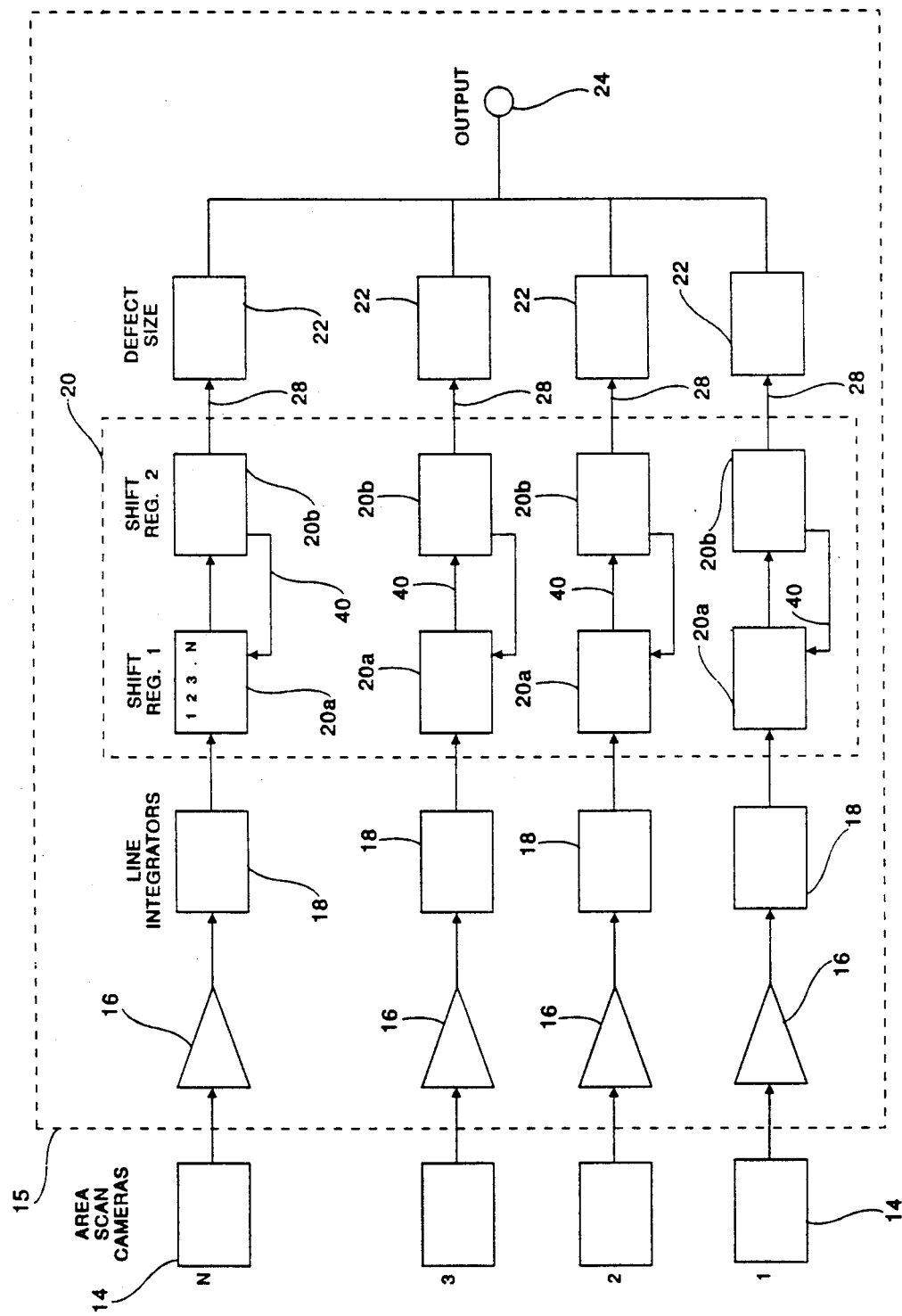
FIG. 4 is a functional block diagram of the processor of the present invention, which processes signals from the CCD cameras to generate an output digital signal.

Referring now also to FIG. 4, there is shown a block diagram of the processor 15 of the present invention, which processes data in parallel from each of the plurality of cameras 14. Since CCD camera 14 is of the standard interlaced type, a full frame or two fields take approximately 0.033 seconds to read out to the output of camera 14. To camera 14 is connected an amplifier 16, which receives the video signals along with undesirable control signals, and in turn generates an amplified signal to a line finder or integrator 18, described in greater detail hereinbelow.

Line integrator 18 integrates each line separately over its time constant (ramp), a period of 63.5 $\mu$seconds. In other words, each line of pixels or photo-sites starting at the top left hand of the picture is shuttled and eventually displayed in 63.5 $\mu$seconds. The final output reaches an energy level that represents the sum of energy received by the individual pixels from the reflected and/or transmitted light of the target web 10.

Integrator 18 is forced by a reset signal to zero and begins to integrate each successive line after the present line has been integrated. The integrated signal is then applied to a sample and hold circuit or time-domain Finite Impulse Response (FIR) filter, shown generally as reference numeral 20. FIR filter 20 includes a first shift and hold register 20a having eight stages and a second shift and hold register 20b, within which is generated control pulses 40 for register 20a. Also part of shift and hold register 20a is a differential amplifier described hereinbelow. The signal output from FIR filter 20 is applied to a defect size circuit 22, which sorts the defect into one of three predetermined size categories: wide (approximately 8 mils), medium (approximately 4 mils), and narrow (approximately 2 mils) in the preferred embodiment. The signals from each defect size circuit 22 are combined together, resulting in a digital output signal 24.

Figure 5:
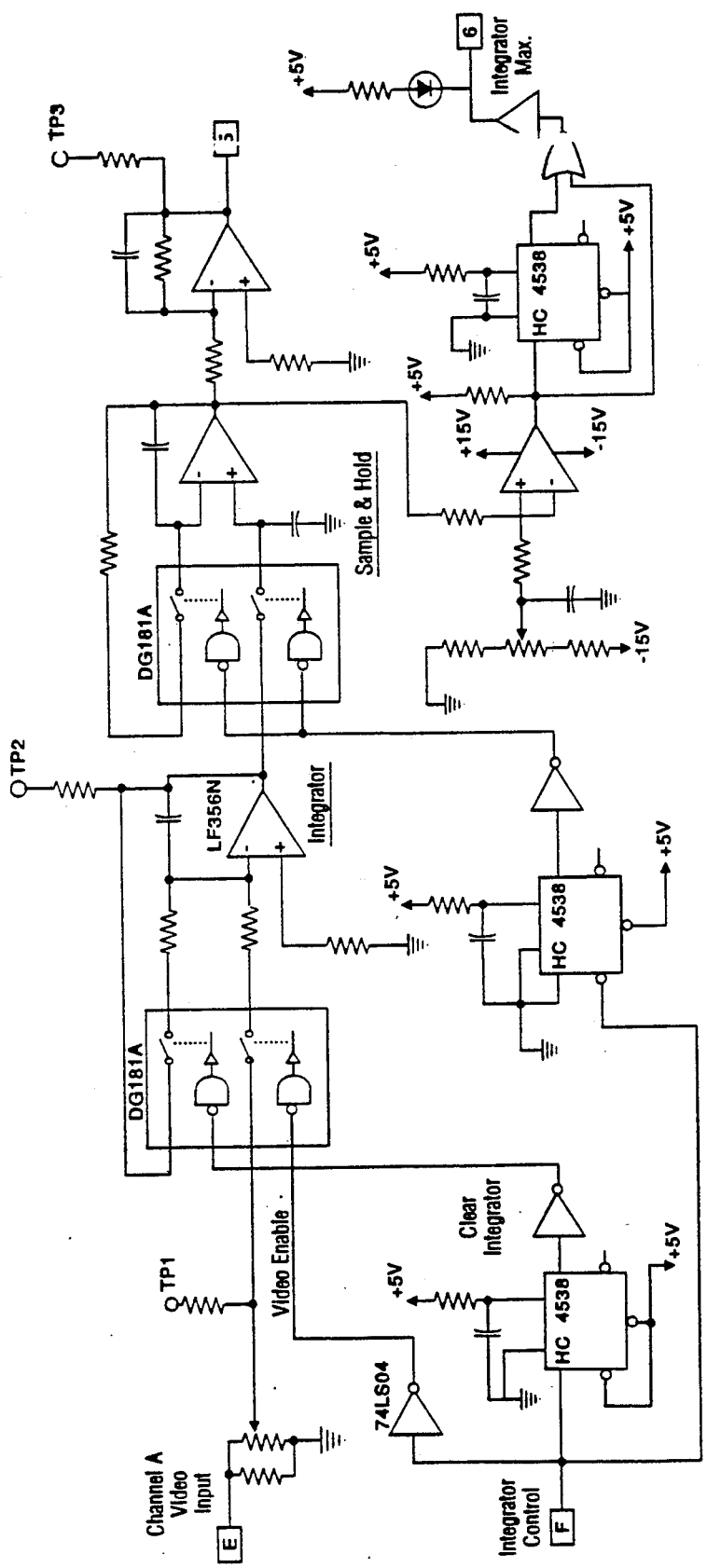
FIG. 5 is a schematic diagram of the line finder integrator in accordance with the present invention.

Line finder (integrator) 18 is shown, along with associated switches and control circuitry, in greater detail in FIG. 5.

Figure 6A:
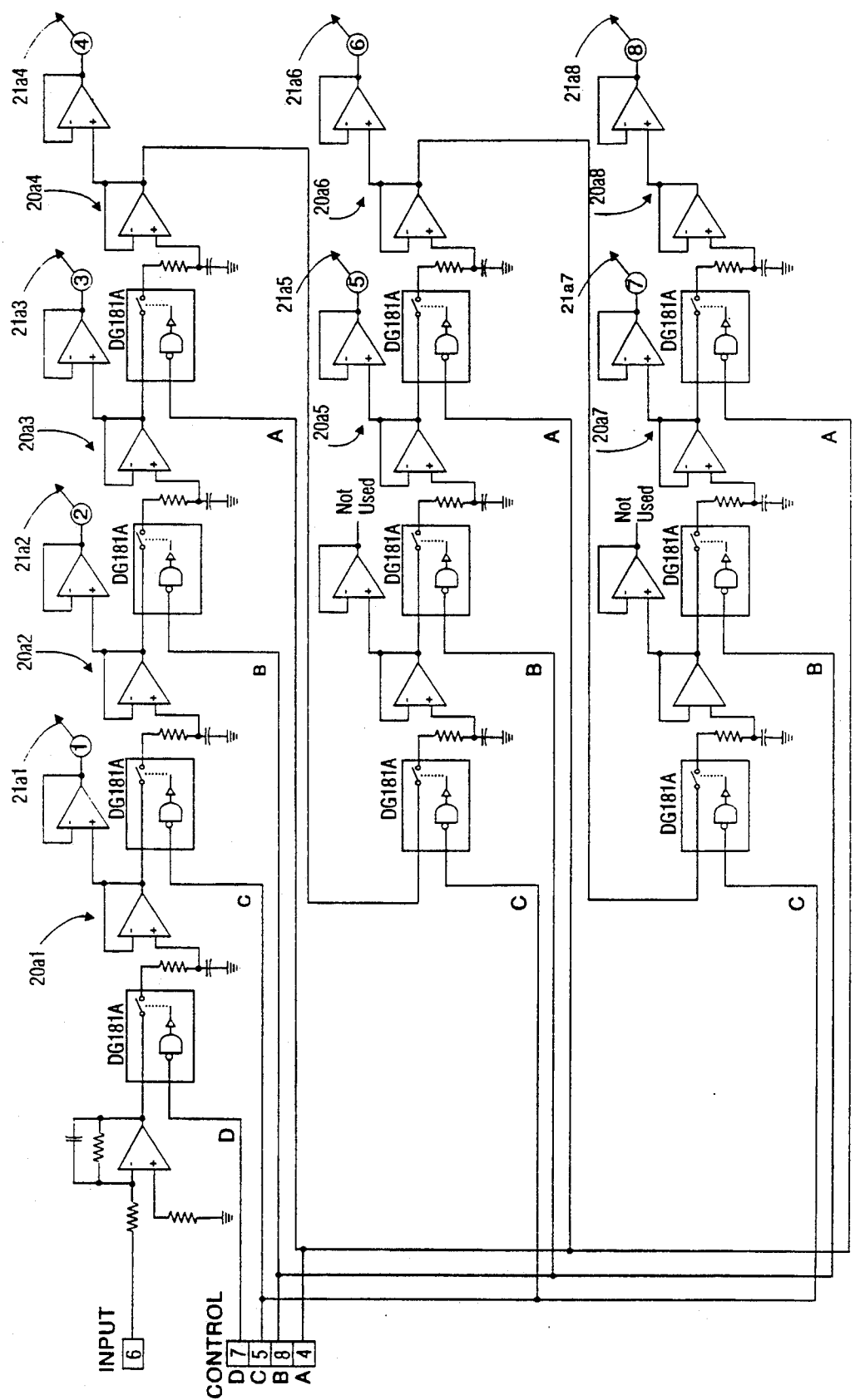
FIG. 6a is a schematic diagram of the shift registers of FIG. 4 and associated taps.

Referring now also to FIG. 6a, there is shown a schematic diagram of the FIR filter 20 of FIG. 4 in greater detail. The system determines the average light over each TV line by integrating the video analog voltage and forming a value representative of intensity for each TV line. The peak values of the integrated TV lines are then sampled and held to form a continuous analog voltage over the picture fields. The sampled waveform is then an envelope of the light over the picture field derived from individual values from the TV lines.

Shift and hold register 20a is actually eight separate register stages 20a1-20a8 in the preferred embodiment. At the end of each line, FIR filter 20 receives the integrated value from integrator 18 and the signal is inserted into shift register 20a1 in serial fashion. An output or tap 21a1-21a8 is associated with each shift register 20a1-20a8, which represents a value of the integrated line level. Parallel output taps along the delay line (i.e., stages 20a1-20a8) each have progressively more time delay.

Figure 6B:
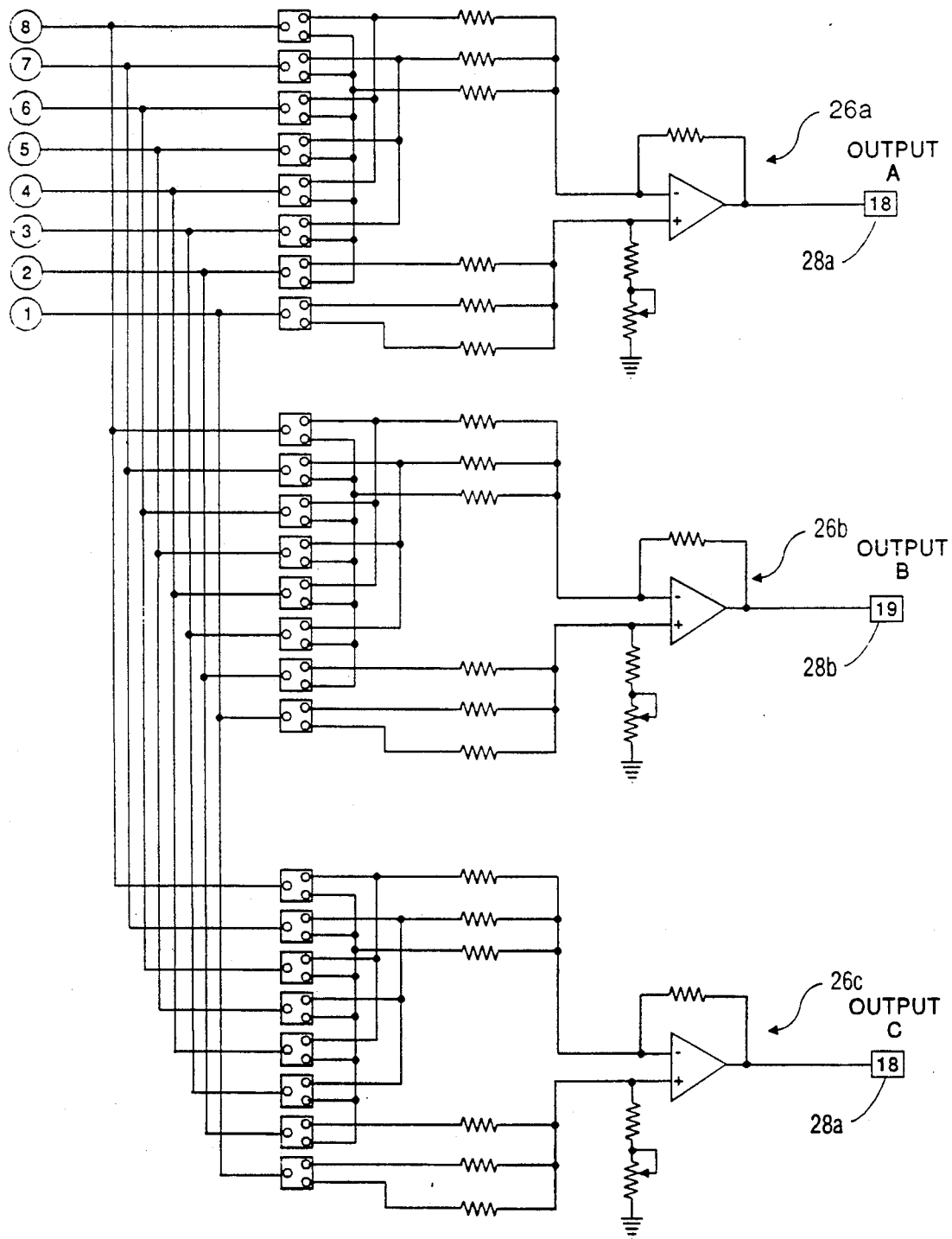
FIG. 6b is a schematic diagram of three potential outputs to allow for three different time delay settings.

Referring now also to FIG. 6b, the taps 21a1-21a8 are used as programming inputs, in one or more pairs, to a differential summing amplifier 26a, 26b, 26c, which is connected to one of the shift register stages 20a1-20a8 with the other input of differential amplifier 26a-26c always connected to the last shift register stage 20a8, so that the last line (N) in camera 14 is summed respectively and sequentially with either of the eight registers 20a1-20a8. The output of differential amplifier 26a-26c is a signal 28a-28c representative of defect values, which is then categorized by defect size circuit 22 (FIG. 4).

Figure 7A:
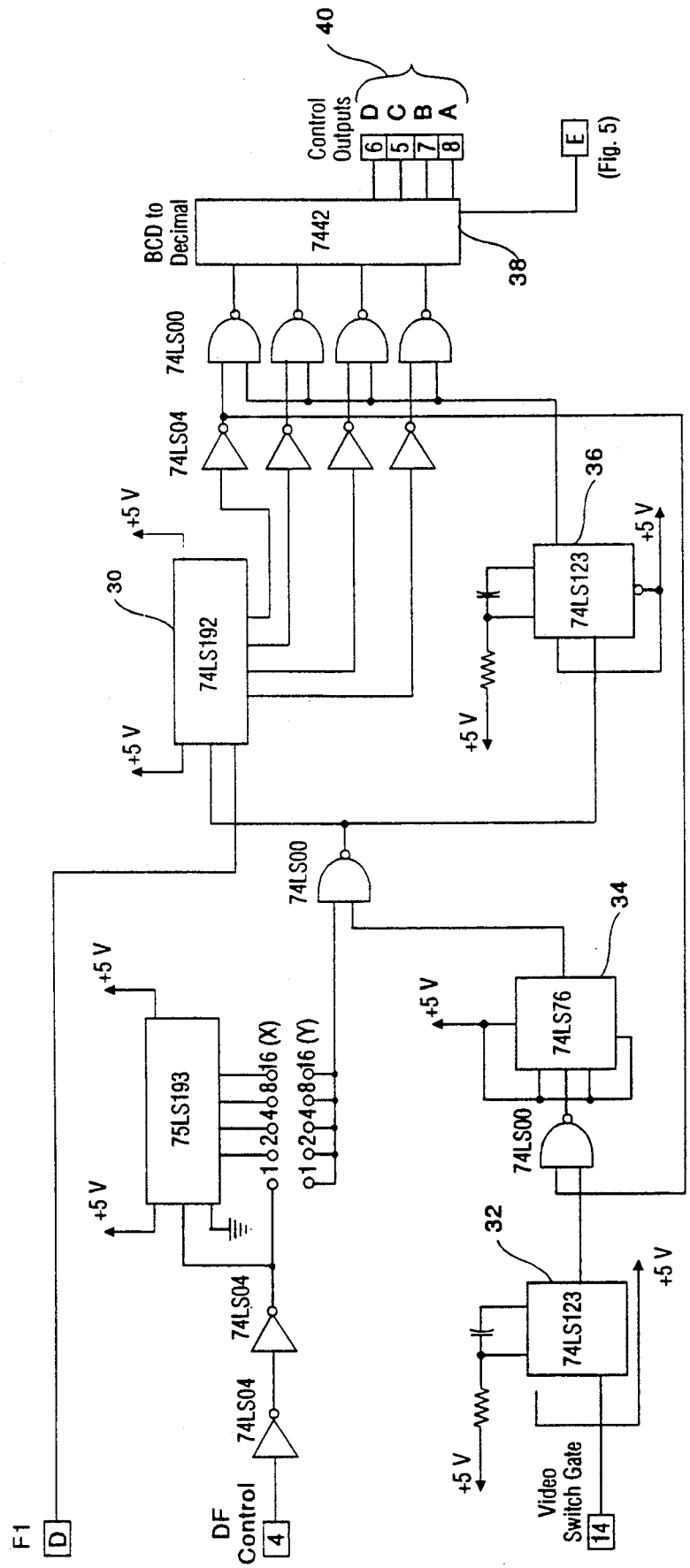
FIG. 7a is a schematic diagram showing the generation of control signals for shift registers.

Referring now also to FIG. 7a, there is shown the first stage of shift and hold register 20b (FIG. 4). The value in the last shift register 20a8 is moved along by bursts of control signals generated by counter 30, flip flops 32 and 34, and one-shot 36 as shown in the figure. A BCD-to-decimal converter 38 produces the digital output control signal 40 applied to shift and hold register 20a. Specifically, ten 2-$\mu$second pulses are used and are spaced apart every 63.5 $\mu$seconds. The ten 2-$\mu$second pulses represent each of the eight shift register stages 20a1-20a8 plus two redundant control lines, A, B, C, D, labelled "Not Used" in FIG. 6a.

Figure 7B:
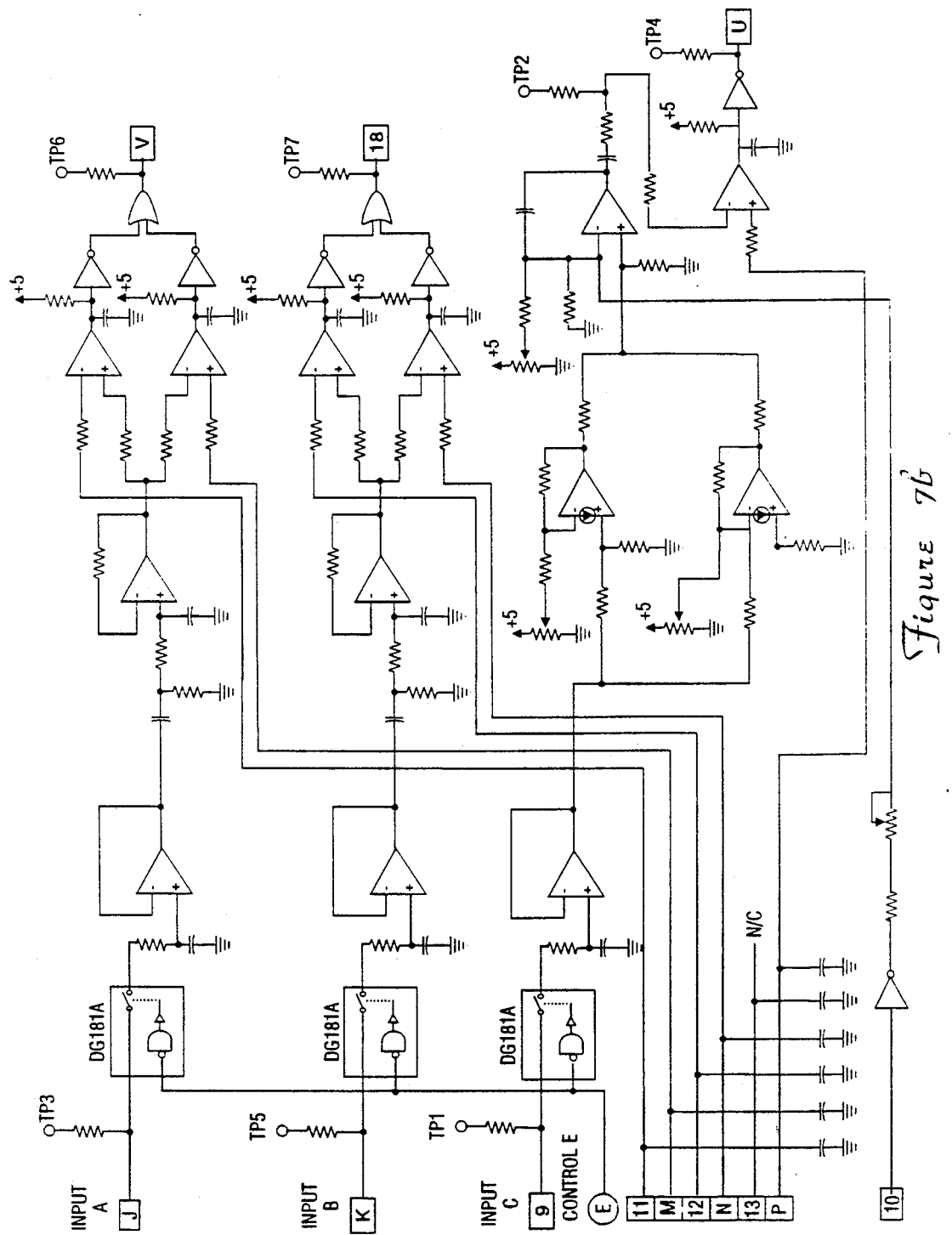
FIG. 7b is a schematic diagram of the output stages of the FIR filter via voltage comparator levels.

Referring now also to FIG. 7b, there is shown the output stage of shift and hold register 20b (FIG. 4). Comparators are used to compare the signals to 5 volt reference voltages as shown in the figure.

By utilizing line integrators with a 63.5 $\mu$second ramp 18 and shift and hold registers 20, short term background noise (i.e., material noise), as well as very low frequency noise can be eliminated, thereby enhancing the signal-to-noise ratio of the desired signal that is generated by scratches and coating streaks. Small black spots or other high frequency background noise affects only a few photo-sites, normally less than 1% of the total integrated value of the 575 photo-sites. A defect, being a scratch or streak running parallel with the lines of scanned photo-sites, is longer than the field of view. Therefore, it affects all of the photo-sites along that particular TV line.

Figures 8A, 8B:
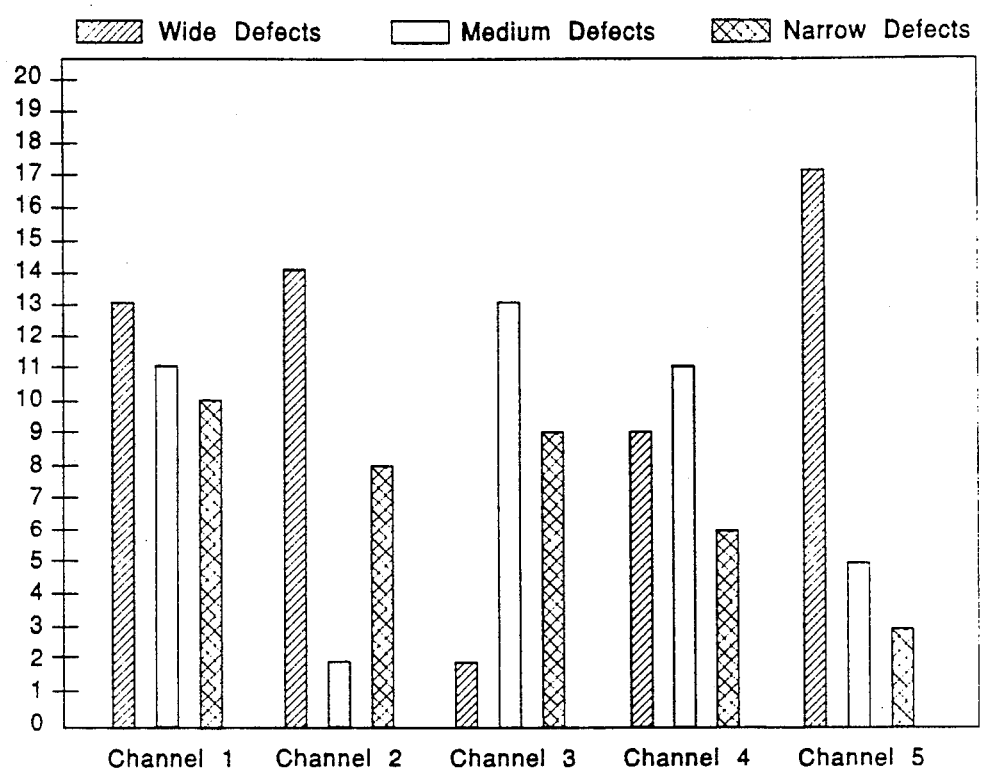
FIGS. 8a–8c depict sample displays associated with the present invention.

Referring now also to FIG. 8a, a bar graph display is shown to depict the number and width of defects over a predetermined length of web. In the preferred embodiment, colors are used to differentiate defect severity. Each channel represents one or more cameras such that the total wideth of the web is divided into the number of represented channels. For example, 180 equally-spaced cameras, divided into 5 channels, as indicated in the figure, represents 36 cameras per channel. Of course, the channels need not represent an equal number of cameras.

Referring now also to FIG. 8b, a tabular, printed display is shown, depicting number and severity of defects and the starting, ending and total footage location thereof.

Figure 8C:
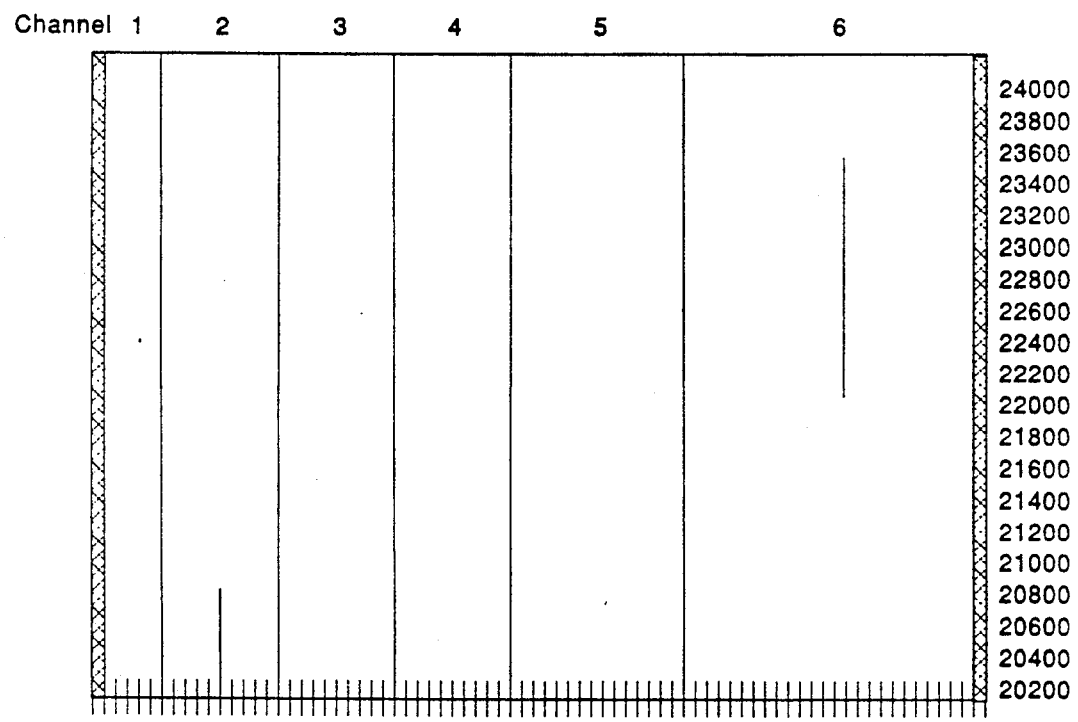

Referring now also to FIG. 8c, there is shown a defect map of the web, wuhich indicates in both analog and digital form, precise locations of defects, relative both to web footage and camera position (x-axis). Severity of defect is shown by differentiated colors (e.g., red represents wide defects; blue represents mdedium defects; and yellow represents narrow defects).

It can be seen that by utilizing the geometry of standard CCD area scan cameras 14 in conjunction with the described circuitry, the invention can detect machine direction type flaws such as coating blade scratches and coating streaks. All requirements for additional optical appendages are eliminated, other than the critical angle between camera and inspected web.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

What is claimed is:

1. A real time system for detecting streaks or scratches on a continuously moving web of material, said real time system being disposed substantially parallel to the direction of motion of said moving web, comprising:
    (a) means defining a feed path along which a web of material moves substantially parallel to a plurality of area scan cameras;
    (b) means disposed adjacent said feed path for impinging electromagnetic energy upon said web of material for reflection back towards said plurality of area scan cameras;
    (c) a plurality of area scan cameras for receiving electromagnetic radiation reflected by said web, dividing the received electromagnetic radiation into separate photo sites, and generating digital video signals in response thereto, said plurality of area scan cameras being disposed adjacent said energy source and web and within 5° of a plane perpendicular to said feed path, said area scan cameras being of the charge coupling device (CCD) type wherein said received electromagnetic radiation is converted into a potential relative to an amount of energy contained in the reflected electromagnetic radiation in a given time frame, which potential is translated into a serial digital output on a photo site by photo site and line by line basis; and
    (d) processing means operatively connected to said area scan cameras for processing said serial digital output to provide analog video signals representing streaks and scratches in said material not readily apparent to eye inspection.

2. The system for detecting streaks or scratches on a web of material in accordance with claim 1, wherein said processing means generates enhanced signal-to-noise ratio signals representative of a streak or scratch upon said web.

3. The system for detecting streaks or scratches on a web of material in accordance with claim 2, wherein said processing means includes means for amplifying, integrating and time-weighting said video signals on a raster-line by raster-line basis.

4. The system for detecting streaks or scratches on a web of material in accordance with claim 3, further comprising means operatively connected to said processing means for combining and displaying said amplified, integrated, time-weighted video signals of each of said plurality of area scan cameras.

5. The system for detecting streaks or scratches on a web of material in accordance with claim 3, wherein said processing means comprises a sample-and-hold circuit for time-weighting said video signals.

6. The system for detecting streaks or scratches on a web of material in accordance with claim 5, wherein said sample-and-hold circuit comprises a finite impulse response (FIR) filter.

7. The system for detecting streaks or scratches on a web of material in accordance with claim 6, wherein said FIR filter comprises storage registers.

8. A real time system for detecting streaks or scratches on a continuously moving web of material, said real time system being disposed substantially parallel to the direction of motion of said moving web, comprising:
    (a) means defining a feed path along which a web of material moves substantially parallel to a plurality of area scan cameras;
    (b) means disposed adjacent said feed path for impinging radiant energy upon said web of material for reflection back towards said plurality of area scan cameras;
    (c) an array of area scan cameras for receiving specular radiation reflected by said web, for dividing the received specular radiation into separate and discrete photo sites, and for generating digital video signals in response thereto, said array of area scan cameras being disposed adjacent said energy source and web and within 5° of a plane perpendicular to said feed path, said area scan cameras receiving said specular radiation and converting said specular radiation into a potential relative to an amount of energy contained in the reflected specular radiation in a given time frame, which potential is translated into a serial digital output on a photo site by photo site and line by line basis; and
    (d) processing means operatively connected to said array of area scan cameras for processing said serial digital output to provide analog video signals representing streaks and scratches in said material not readily apparent to eye inspection.

9. The system for detecting streaks or scratches on a web of material in accordance with claim 8, wherein said processing means includes means for amplifying, integrating and time-weighting said video signals on a raster-line by raster-line basis.

10. The system for detecting streaks or scratches on a web of material in accordance with claim 9, further comprising means operatively connected to said processing means for combining and displaying said amplified, integrated, time-weighted video signals of each of said array of area scan cameras.

* * * * *